(12) United States Patent
Borri

(10) Patent No.: US 8,435,030 B2
(45) Date of Patent: May 7, 2013

(54) ORTHODONTIC BRACES

(76) Inventor: Franco Borri, Cossano Canavese (IT)

(*) Notice: Subject to any disclaimer, the term of this patent is extended or adjusted under 35 U.S.C. 154(b) by 0 days.

(21) Appl. No.: 13/248,812

(22) Filed: Sep. 29, 2011

(65) Prior Publication Data

US 2012/0082949 A1    Apr. 5, 2012

(30) Foreign Application Priority Data

Sep. 30, 2010 (IT) .................. TO2010A0798

(51) Int. Cl.
*A61C 3/00* (2006.01)

(52) U.S. Cl.
USPC ............................................................ 433/6

(58) Field of Classification Search ...... 433/6; 128/861, 128/862
See application file for complete search history.

(56) References Cited

U.S. PATENT DOCUMENTS

| | | | | |
|---|---|---|---|---|
| 3,574,941 A * | 4/1971 | Ritter | .............................. | 433/18 |
| 4,608,974 A * | 9/1986 | Sicurelli, Jr. | .................. | 128/860 |
| 4,609,349 A * | 9/1986 | Cain | ................................. | 433/6 |
| 4,793,803 A * | 12/1988 | Martz | ................................ | 433/6 |
| 6,702,575 B2 * | 3/2004 | Hilliard | ............................ | 433/6 |
| 7,077,646 B2 * | 7/2006 | Hilliard | ............................ | 433/6 |
| 7,810,503 B2 * | 10/2010 | Magnin | ........................ | 128/848 |

* cited by examiner

*Primary Examiner* — Ralph Lewis
(74) *Attorney, Agent, or Firm* — Merchant & Gould P.C.

(57) ABSTRACT

Orthodontic braces including a plaque 2, preferably made of a plastic material for food purposes, on which there is reproduced the shape of at least one portion of the palatal-dental arch, both top and bottom, the arch includes at least one tooth (D) of the patient who will be using the braces. The braces include at least one thrust plate 3 adapted for the correction of malocclusions, including at least one inner face 32, in which there is at least one adjustment 33, which is adapted to adjust the thrust exerted on the at least one tooth "D" by at least one outer face 31.

7 Claims, 2 Drawing Sheets

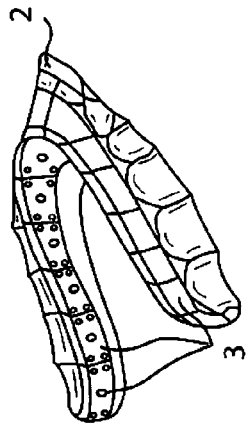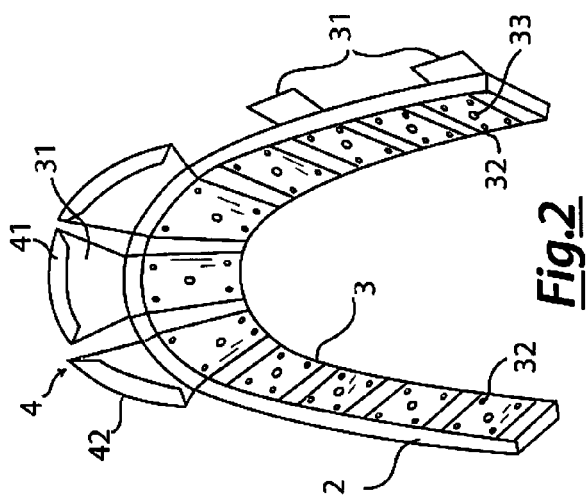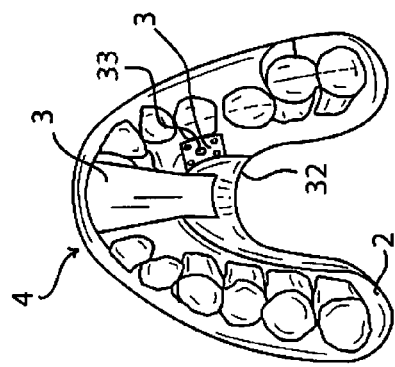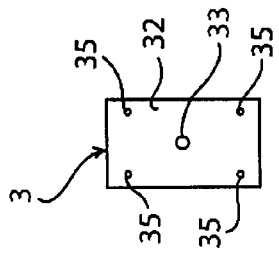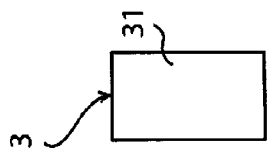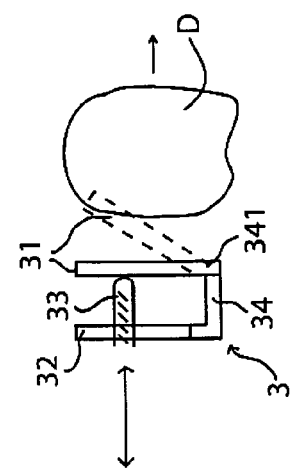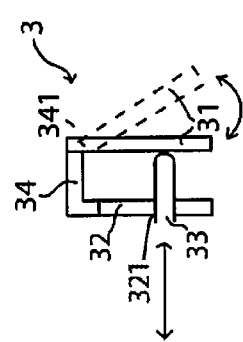

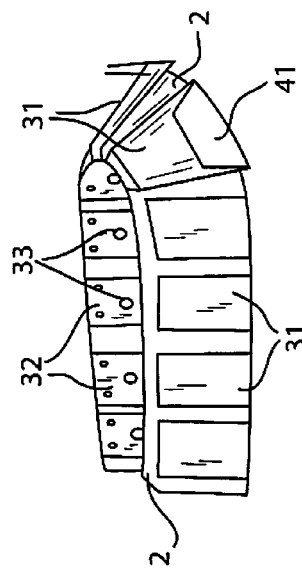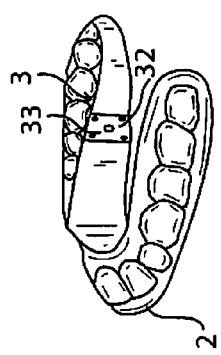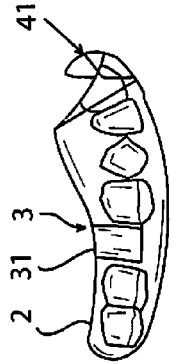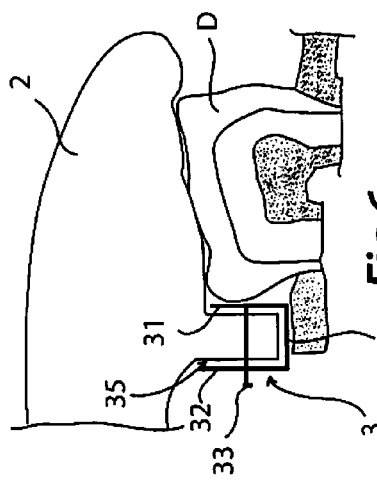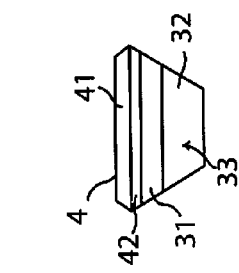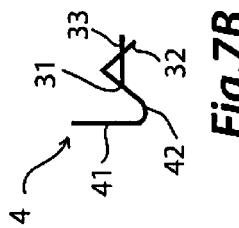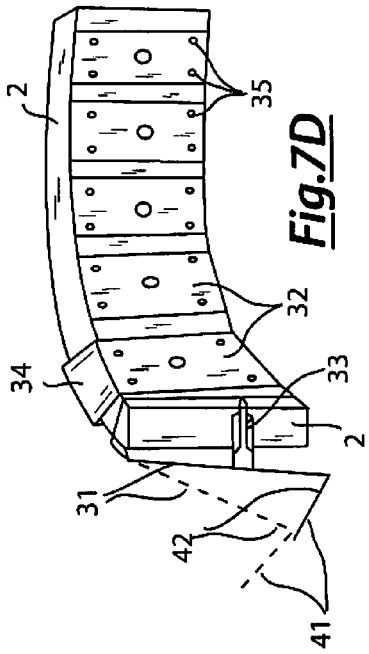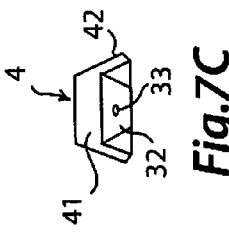

ORTHODONTIC BRACES

This application claims benefit of Serial No. TO 2010 A 000798, filed 30 Sep. 2010 in Italy and which application is incorporated herein by reference. To the extent appropriate, a claim of priority is made to the above disclosed application.

BACKGROUND

The present invention is relative to orthodontic braces, which are mobile, removable and adjustable.

Orthodontic braces are devices used by the orthodontist to help align teeth, in order to obtain a correct mastication, to improve dental health as well as appearance of the smile for people with teeth difects and misalignment of the set of teeth. Normally, orthodontic braces manage to move the teeth in the direction desired.

In the orthodontic industry there are basically three different types of orthodontic braces, i.e.
- fixed braces, which are used to treat misalignments, since they manage to move the teeth in the direction desired;
- mobile braces, which are mainly used in interceptive orthodontics to modify wrong habits and behaviors in the growing and developing child;
- pre-treatment braces, both fixed and mobile, which perform tasks that could not be otherwise performed with other external orthodontic appliances, such as palate expansion or shaping of the jaw.

Normally, fixed braces comprise metal wires, elastics, hooking means, tubings or bands on the molars.

These braces usually make it more difficult for the patients to take care of their own oral hygiene, since said metal wires, elastics and tubings on the molars hinder the correct removal of dental framework from the teeth and make the use of dental floss highly complicated.

Furthermore, these braces turn out to be extremely unaesthetic, since they are very conspicuous and, therefore, not suited to be worn by adult patients.

Mobile braces are normally used to treat less serious malocclusions and for dentofacial deformities, but they normally allow limited movements of the teeth. These movements are normally caused by means of screws, springs and arcs.

The braces of this type allow the creation of a harmonious balance in the lower part of the face both from a functional and from an aesthetic point of view, since they guarantee not only orthodontic results, but also orthopedic results, since they correct and guide the development of the bones.

Pre-treatment braces are appliances which are sometimes invasive and act on the teeth before the use of one of the above-mentioned types of braces.

The most common type of pre-treatment braces is the one that has to be applied on the palate, which is normally called palatal expander and comprises a palatal metal framework with a central hole of reduced dimensions, into which a suited expansion key is inserted, which is adapted to obtain the expansion of the palatal framework.

Fixed braces, as mentioned above, are adapted to treat very serious malocclusions, but they present as a drawback both the difficult oral hygiene and the aesthetic problem.

In order to solve the above-mentioned problems connected with the oral hygiene and the aesthetic aspect, orthodontists normally suggest the use of mobile braces.

Such mobile braces, though, are only adapted to treat minor malocclusions.

If mobile orthodontic braces are used to treat more serious malocclusions, they need much more time in order to reach the desired movements of the teeth; furthermore, as time goes by and the treatment goes on, it is periodically necessary to modify the shape of the braces themselves, often causing an actual replacement of the braces with new ones with a consequent increase of the costs for the patient.

SUMMARY

An aspect of the present invention is to solve the above-mentioned problems by providing mobile and adjustable orthodontic braces, adapted to treat malocclusions and correct labioversions and whose shape can be modified without the need to replace the braces with new ones as the treatment goes on.

Such braces can be customized through the dental cast of the patient or they can be universally adjustable, so that they can be applied to any dental arch without the need to obtain the dental cast of the patient who will be using the braces.

BRIEF DESCRIPTION OF THE DRAWINGS

The additional features and advantages of said orthodontic braces will be better understood from the following detailed description of a specific embodiment with reference to the accompanying drawings, which specifically illustrate what follows:

FIG. 1 shows, from a top view, mobile braces for malocclusions according to the present invention with thrust plate and corrective hook for the traction of the maxillary incisors in labioversion;

FIG. 2 shows, from a top view, mobile braces for malocclusions according to the present invention in an alternative embodiment;

FIG. 3 shows, from a side view, universal braces for the top dental arch, which are totally adjustable;

FIGS. 4A, 4B, 4C and 4D show side views of a correction plate comprised in the braces according to FIG. 1 in two different embodiments;

FIGS. 5A, 5B and 5C illustrate the side views of a further embodiment of the present invention, which is adapted to the treatment of malocclusions and/or labioversions;

FIG. 6 shows a cross-section view of the action of the thrust plate as per FIGS. 4A, 4B and 4C on a tooth;

FIGS. 7A, 7B, 7C and 7D illustrate side views of a corrective hook for the treatment of labioversions of the incisors and, in particular, FIG. 7D shows a cross-section view of the hook applied to the braces.

DETAILED DESCRIPTION

With reference to the above-mentioned figures, the orthodontic braces according to the present invention comprise a framework 2, preferably made of a food compliant plastic material, on which there is reproduced the shape of at least one portion of the palatal-dental arch, both top and bottom. Said arch comprising at least one tooth D of the patient who will be using said braces.

Said braces comprise, furthermore, at least one thrust plate 3 adapted for the correction of malocclusions, comprising at least an inner face 32, in which there is comprised at least an adjustment means 33, which is adapted to adjust the thrust exerted on said at least one tooth D by means of at least an outer face 31.

Said thrust plate 3 is fitted to framework 2 preferably flush with framework 2 itself, thus creating mobile and adjustable orthodontic braces according to the feature of the present invention.

Preferably, the hollow space created between inner face 32 and outer face 31 is engaged by a portion of framework 2, so as to allow thrust plate 3 to be fitted to framework 2.

Thrust plate 3 is preferably fixed by means of a plurality of fastening means 35, e.g. nails, which, for example, fit inner face 32 to framework 2.

The material of which thrust plate 3 is adapted to guarantee both an adequate resistance for succeeding, in time, in correctly positioning one tooth or more teeth, and a suited flexibility, so as to allow the adjustment of the thrust against said one tooth or more teeth; thrust plate 3 being made of plastic or metal material.

In the embodiment described in FIGS. 4A, 4B, 4C and 4D thrust plate 3 preferably has a U-shape as in FIG. 4A or an upside-down U-shape as in FIG. 4B, inner face 32 and outer face 31 being divided by at least one connection portion 34.

Adjustment means 33, in the embodiments illustrated in FIGS. 4A and 4B, passes through inner face 32 by means of at least a hole 321.

The progressive insertion of adjustment means 33 into inner face 32 increases the force exerted on outer face 31, which, in turn, acts on said at least one tooth D comprised in the malocclusion to be treated.

Connection portion 34 preferably presents, in the joint with outer face 31, a connection section 341 made of a material presenting stronger flexibility features then the rest of thrust plate 3, so as to allow the movement of outer face 31 as a function of adjustment means 33. The movement of adjustment means 33 is preferably determined and ensured by a threaded portion applied for example to hole 321, so that the forward movement of adjustment means 33, which in this example in present in form of a screw, can be determined as a function of the pitch of the threaded portion.

The action of adjustment means 33 on outer face 31 causes the latter to bend at an angle that is proportional to the introduction of adjustment means 33 itself into inner face 32.

Said thrust plates 3 are arranged inside framework 2 in correspondence to one tooth or more teeth that have to be moved in order to treat malocclusions.

Each thrust plate 3 is properly adjusted, for example by the orthodontist, so as to create personal mobile braces, which, unlike what normally happens, do not need to be completely replaced as the dental treatment goes on, since said braces can be instantaneously adjusted, thus allowing a treatment of the dental problems involved following step-by-step the changes of the dental arch, without the need to replace the braces being used with new ones.

The embodiment shown in FIG. 4B also allows, besides the treatment of malocclusions, an easy positioning of the braces themselves, thus preventing, for example, the braces of the top dental arch from sliding.

In an alternative embodiment, adjustment means 33 is a self-tapping screw, which engages the portion of framework 2 interposed between inner face 32 and outer face 31, keeping the position desired and going on acting on the outer face 31.

In a further embodiment, thrust plate 3 performs the function of connection portion 34 comprised in the embodiment described above, since it fixes inner face 32 to outer face 31 by means of one or more adjustment means adapted to adjust the force to be applied.

In said embodiment outer face 31 moves parallel to inner face 32.

Said brases can comprise, furthermore, one or more corrective hooks 4, which are properly fitted to thrust plate 3.

Each corrective hook 4 has such a shape that allows the treatment of malocclusions, such as labioversions of the maxillary incisors; furthermore, each corrective hook 4 performs a function of support of the braces, thus allowing the correct positioning of the braces themselves.

Said corrective hook 4 comprises at least an outer portion 41 and an enveloping portion 42, which cooperate with each other and, by so doing, allow, as mentioned above, both the treatment of malocclusions and labioversions and the correct positioning of the braces.

Enveloping portion 42 is connected, at one end, to outer face 31 of thrust plate 3 and, at the other end, to outer portion 41 of corrective hook 4, so as to create a continuous structure.

Said enveloping portion 42 surrounds at lest one portion of tooth D which has to undergo the treatment.

The corrective action of said corrective hook 4 on at least one tooth D takes place, like in the case of thrust plate 3 described above, by acting on adjustment means 33, which, by pushing on outer face 31, where said corrective hook 4 is connected, acts on tooth D until a force suited for the treatment is reached.

In alternative embodiments that are not illustrated, corrective hook 4 can be used for the treatment of labioversions not only on incisors, but also on other teeth in the frontal part of the dental archs.

Said corrective hook 4 preferably has such dimensions that allow it to simultaneously act on two teeth D, so as to more easily make the dental arch uniform.

Outer portion 41 is preferably shaped so as to act on the following pairs of teeth D:
  central incisors;
  left lateral incisor and left canine;
  right lateral incisor and right canine.

In a further embodiment, corrective hook 4 is applied to a plate 3, which does not comprise adjustment means 33. This latter solution is only used for the correction of labioversions and performs, furthermore, a support function for the braces on the dental arch; to this aim, this solution comprises an adjustment means, which allows said hook 4 to be adjusted to the dental arch, so as to fulfill the support function.

In the embodiment shown in FIGS. 1 and 3, there are illustrated frameworks 2 that reproduce the cast of the whole dental arch; FIG. 3 illustrates, in particular, the top dental arch and FIG. 1 illustrates, in particular, the bottom dental arch.

FIG. 2 illustrates an alternative embodiment of the braces, in which framework 2 presents reduced dimensions and there is no cast of the dental arch.

In further alternative embodiments it is possible to provide a framework 2 that reproduces the cast of a single portion of dental arch: said framework comprising at least one corrective hook 4, which, besides performing the correction function, is also adapted to help position framework 2 itself and keep it in the right position, without the need to intervene on the patient with the insertion of hooks for supporting the braces.

In order for said corrective hook 4 to perform the function of support for the upper portion of the braces, the corrective hook is preferably arranged in correspondence to the lateral incisor and the canine both of the right-hand portion and of the left-hand portion of the top dental arch.

This solution allows the braces to be held in the correct position, even when the dental pathology to be treated, instead of a labioversion, is a regression of the tooth.

For reasons of support and in order to help the patient to position the device, the framework is preferably made for the whole dental arch, top and/or bottom, and presents a plurality of support portions, such as, for instance, corrective hooks 4 used only for support purposes.

Preferably, the support portions are made, furthermore, of portions of framework 2, which act on the teeth and/or on the palate, so that the braces cannot modify their position; this applies, above all, to braces used to correct malocclusions in the top dental arch.

In a further alternative embodiment, framework 2 reproduces the cast of both dental arches, thus allowing the simultaneous treatment of different malocclusion both on the top arch and on the bottom arch.

In the embodiment illustrated in FIG. 3, there is a plurality of thrust plates 3 arranged on the framework, e.g. one plate 3 in correspondence with each tooth, so that the braces turn out to be universal and adjustable to any malocclusion, without the need for framework 2 to exactly reproduce the dental cast of the patient who will be using the braces.

The embodiment illustrated in FIG. 1 shows the presence of a thrust plate 3, which simultaneously acts on two teeth using a single adjustment means 33.

The combination of said corrective hook 4 of thrust plate 3 and of the support portions allows the correct positioning and the support of the braces according to present invention in the dental arch.

The invention claimed is:

1. Orthodontic braces, comprising:
   a framework made of food contact compliant plastics, reproduced on which is at least a shape of at least one portion of a whole palate-dental arch, both top or bottom, said arch comprising at least one tooth of a patient for whom said braces are designed;
   a plurality of thrust plates, including one of the thrust plates for each tooth, for correction of malocclusions, each of said thrust plates comprising:
      at least a first face and at least a second face, regulating means, for regulating thrust exerted on said at least one tooth by said second face; said second face being connected to the first face and both the first face and the second face being fitted to said framework;
      one or more corrective hooks fixed to the second face of the thrust plate, said corrective hook comprising at least one first portion and one enveloping portion; said enveloping portion being connected between said second face and said first portion; said corrective hook being configured to surround at least a portion of the tooth to support the braces and to provide for treatment of malocclusions, labioversions and mandibular regressions.

2. The braces according to claim 1, wherein the first face and the second face are connected by at least one U-shaped connection portion of the thrust plate fixed to the framework.

3. The braces according to claim 2, wherein said thrust plate is positioned flush with said framework and covering a part thereof.

4. The braces according to claim 2, wherein the regulating means, which act on the outer plate pass through the first face through at least one hole.

5. The braces according to claim 4, wherein progressive insertion of the means within the first face increases force exerted on the outer face, which in turn acts on the at least one tooth in the malocclusion to be treated.

6. The braces according to claim 1, wherein the shape reproduced on the framework reproduces a dental cast of the patient.

7. The braces according to claim 1, wherein the one or more corrective hooks is set in a position corresponding to a lateral incisor and a canine both of a right-hand portion and of a left-hand portion of a top dental arch when the one or more corrective hooks support a top portion of the braces.

* * * * *